United States Patent
Fourtillan et al.

[11] Patent Number: 6,140,372
[45] Date of Patent: Oct. 31, 2000

[54] ACYL DERIVATIVES OF MELATONIN AND OF MELATONINERGIC ANALOGUES AND THEIR USE AS MEDICINAL PRODUCTS

[75] Inventors: Jean-Bernard Fourtillan; Marianne Fourtillan, both of Migne-Auxances; Jean-Claude Jacquesy, Buxerolles; Marie-Paule Jouannetaud, Poitiers; Bruno Violeau, Marcay; Omar Karam, Poitiers, all of France

[73] Assignee: Cemaf and Laboratories Besins Isovesco S.A., France

[21] Appl. No.: 09/292,968

[22] Filed: Apr. 16, 1999

Related U.S. Application Data

[62] Division of application No. 09/011,042, filed as application No. PCT/FR96/01260, Aug. 7, 1996, Pat. No. 6,004,991.

[30] Foreign Application Priority Data

Aug. 8, 1995 [FR] France ................................ 95 09611

[51] Int. Cl.[7] .................. A61K 31/165; A61P 25/20; C07C 233/25; C07C 233/33; C07C 235/68
[52] U.S. Cl. .................. 514/630; 514/629; 564/123; 564/194; 564/219; 564/222
[58] Field of Search .................. 514/613, 630; 564/123, 219, 222

[56] References Cited

U.S. PATENT DOCUMENTS

| | | | |
|---|---|---|---|
| 5,276,051 | 1/1994 | Lesieur et al. | 514/415 |
| 5,318,994 | 6/1994 | Andrieux et al. | 514/613 |
| 5,403,851 | 4/1995 | D'Orlando et al. | 514/364 |
| 5,525,442 | 6/1996 | Andrieux et al. | 514/613 |

FOREIGN PATENT DOCUMENTS

| | | |
|---|---|---|
| 0 527 687 A2 | 3/1994 | European Pat. Off. . |
| 0 585 206 A1 | 3/1994 | European Pat. Off. . |

*Primary Examiner*—Joseph McKane
*Assistant Examiner*—Jane C. Oswecki
*Attorney, Agent, or Firm*—Finnegan, Henderson, Farabow, Garrett & Dunner

[57] ABSTRACT

The invention relates to derivatives of general formula I

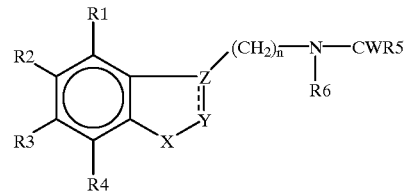

as defined in the description.

The invention also relates to a process for their preparation and to their therapeutic use, in particular for the treatment of complaints associated with melatonin disorders, and pharmaceutical and cosmetic compositions comprising them.

4 Claims, No Drawings

ACYL DERIVATIVES OF MELATONIN AND OF MELATONINERGIC ANALOGUES AND THEIR USE AS MEDICINAL PRODUCTS

This is a division of application Ser. No. 09/011,042, filed Mar. 27, 1998 now U.S. Pat. No. 6,004,991, which is the National Phase filing of PCT/FR96/01260 filed Aug. 7, 1996, all of which are incorporated herein by reference.

The present invention relates to novel melatoninergic agonist derivatives, to a process for their preparation and to their use as medicinal products.

Melatonin, N-acetyl-5-methoxytryptamine, is a hormone of the pineal gland, isolated by Lerner et al. (J. Am. Chem. Soc. 80, 1958, 2587), which has formed the subject of many studies for its circadian activity, in the rhythm of sleep, for its effects on the production of testosterone, for its activity on the hypothalamus and in psychiatric disorders.

It has thus been envisaged to employ melatonin and analogues thereof, especially for the treatment of depression and psychiatric disorders, in particular stress, anxiety, depression, insomnia, schizophrenia, psychosis and epilepsy, and also for the treatment of sleeping disorders associated with travelling ("jet lag"), neurodegenerative diseases of the central nervous system such as Parkinson's disease or Alzheimer's disease, for the treatment of cancers, or alternatively as a contraceptive or as an analgesic.

However, the direct use of melatonin in vivo has not proved to be very satisfactory, given that a first passage through the liver extracts more than 90% of the active principle when it is administered orally.

Various melatonin analogues have been described, demonstrating two routes of research which relate either to the substituents of melatonin (WO-A-89/01472, U.S. Pat. Nos. 5,283,343, 5,093,352 or WO-A-93/11761) or to the aromatic ring by replacing the indolyl group by a naphthyl group (FR-A-2 658 818, FR-A 2 689 124).

The present patent application proposes a novel route of development of melatonin analogues having improved activity.

The present invention thus relates to novel derivatives of general formula I

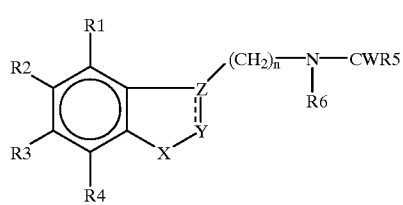

I in which
W represents an oxygen or sulphur atom or a radical= $NR_{12}$, $R_{12}$ being a hydrogen atom or a lower alkyl, aryl, lower aralkyl or cycloalkyl radical
X represents a divalent radical of formula $N-R_7$ or $-CR_{13}=CR_{14}-$ or $CR_{15}R_{16}-CR_{17}R_{18}-$
Y—Z represents a trivalent radical of formula $CR_8=C$, $CW-CR_{19}$, W having the same definition as above or $CR_{20}R_{21}-CR_{19}$
or
X—Y—Z represents $-CR_{15}R_{16}-CR_{22}=CR_{23}-CR_{19}$ or $-CR_{15}R_{16}-CW-CR_{24}R_{25}-CR_{19}$ or $-CR_{15}R_{16}-CR_{17}R_{18}-CW-CR_{19}$ W having the same definition as above
n represents an integer between 1 and 4, preferably 2,
R1 to R6, R15 to R21, R24 and R25 representing, independently of each other, a hydrogen atom, a hydroxyl radical or a lower alkyl, cycloalkyl, lower alkoxy, aryloxy, lower aralkoxy, (lower)alkylthio, arylthio, (lower)aralkylthio, halo or nitro radical or an unsaturated aliphatic, lower alkenyl, lower alkinyl, lower alkyl, aryl or aralkyl chain, each optionally substituted with one or more hydroxyls, with one or more halogens, a lower perhaloalkyl radical, an amino, (lower)alkylamino, (lower)dialkylamino, arylamino, diarylamino, aralkylamino or arylalkylamino radical, a radical of the form $CV-R_{11}$ or $QCVR_{11}$, in which V represents an oxygen or sulphur atom or an imine radical=$N-R_{12}$, $R_{11}$ has one of the meanings of $R_1$,
Q represents an oxygen or sulphur atom on condition that R15 and R16, R17 and R18, R20 and R21, and R24 and R25 cannot simultaneously be a hydroxyl radical, or an amine, or a hydroxyl and an amine, a hydroxyl and a halogen, or a hydroxyl and an alkoxy,
R7 has one of the meanings of R1 except that it cannot be hydroxyl, but it can represent the radical $SO_2R_{26}$, $R_{26}$ being an alkyl or lower haloalkyl radical, in particular $CF_3$,
R13 and R14, independently of each other, have one of the meanings of R1 except that when Y—Z represents $CR_{20}R_{21}-CR_{19}$, they cannot be an amino, (lower)alkylamino, hydroxyl, arylamino, aralkylamino or arylalkylamino radical,
R22 and R23, independently of each other, have one of the meanings of R1 except that when X—Y—Z is of the form $CR_{15}R_{16}-CR_{22}=CR_{23}-CR_{19}$, they cannot be a hydroxyl, amino, (lower)alkylamino, arylamino, aralkylamino or arylalkylamino radical,
R8 has one of the meanings of R1 and may also represent a halogen atom (chlorine, bromine, iodine or fluorine), or a group $Q-CV-R11$ in which Q, V and R11 are as defined above, or
R5 and R5 together form part of a ring of formula $-(CH_2)_m-CW-$, m being an integer between 2 and 3, and W defined above, on condition that at least one of R1, R6, R7 or R8, R20, R21, R23, R24 and R25 represents a (lower)alkylcarbonyl or radical a (lower) alkylthiocarbonyl, their racemic mixtures, their pure enantiomers or their mixtures in all proportions, and their therapeutically acceptable salts.

The present invention also relates to novel derivatives of general formula I

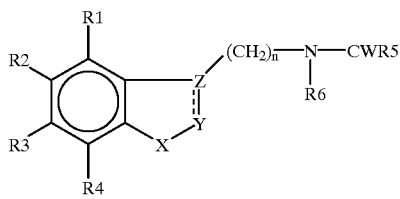

I in which
W represents an oxygen or sulphur atom
X represents a divalent radical of formula $N-R_7$ or $-CH=CH-$
Y—Z represents a divalent radical of formula $CR_8=C$, $CO-CH$ or $CS-CH$
n represents an integer between 1 and 4, preferably 2,
R1, R2, R3 and R4 represent, independently of each other, a hydrogen atom, a hydroxyl radical or a lower alkyl, lower alkoxy, aryloxy, lower aralkoxy, halo or nitro radical, R5 represents a hydrogen atom or a lower alkyl, aryl or lower aralkyl radical, each optionally substituted with one or more halogens, a lower perhaloalkyl radical, an amino, (lower)alkylamino or (lower)dialkylamino radical or a lower alkoxy radical, R6, R7 and R8 represent, independently of each other, a hydrogen atom, a lower alkyl, aryl or lower aralkyl radical or a radical of the form CV—R11, in which V represents an oxygen or sulphur atom and R11 a hydrogen atom or a lower alkyl, aryl, lower aralkyl or cycloalkyl radical, an alkyl substituted with one or more halogens, if V is an oxygen atom, R11 may also represent a lower alkoxy, a lower alkylthio, an amino radical, a (lower) alkylamino or a (lower) dialkylamino, or R8 may also represent a halogen atom (chlorine, bromine, iodine or fluorine), a group Q—CV—R11 in which Q represents an oxygen or sulphur atom, and V and R11 are as defined above, or R5 and R6 together form part of a ring of formula —$(CH_2)_m$—CW—, m being an integer between 2 and 3, and W defined above, on condition that at least one of R6, R7 or R8 represents a (lower) alkylcarbonyl radical or a (lower) alkylthiocarbonyl, their racemic mixtures, their pure enantiomers or their mixtures in all proportions, and their therapeutically acceptable salts.

The expression lower alkyl, alkoxy or perhaloalkyl is generally understood to refer to radicals whose alkyl residue comprises between 1 and 6 carbon atoms.

These are preferably linear or branched $C_1$–$C_4$ alkyl residues chosen more particularly from methyl, ethyl, n-propyl, i-propyl, n-butyl, i-butyl or t-butyl groups.

The term cycloalkyl refers to optionally substituted $C_3$–$C_6$ rings.

The term aryl generally denotes aromatic and heteroaromatic groups, in particular aryls chosen from phenyl, thienyl, furyl, pyridyl or naphthyl groups.

The aryl radicals may also be substituted with one or more substituents chosen in particular from the lower alkyl, lower alkoxy or halo radicals defined above.

The term lower aralkyl will be understood to refer to the combination of a lower alkyl and an aryl as defined above. This will preferably be the optionally-substituted benzyl radical.

The halo radicals are preferably chosen from fluorine, chlorine, bromine or iodine atoms.

The perhalo radicals are preferably perfluoro radicals.

When the derivatives according to the invention comprise at least one asymmetric carbon of R or S configuration, the present invention also relates to the racemic mixtures of the general formula I, as well as its pure enantiomers, or their mixtures in all proportions.

The therapeutically acceptable salts of the derivatives according to the invention are the usual organic or inorganic salts of the art, in particular the hydrochlorides, tosylates, mesylates and citrates, as well as the solvates such as the hydrates or hemihydrates of the compounds of general formula I.

The present invention relates more particularly to the derivatives of general formula I for which W represents an oxygen atom and n is equal to 2.

Advantageously, at least one of the substituents R2 or R3 is other than a hydrogen atom and preferably represents a hydroxyl or lower alkoxy radical, in particular a methoxy radical.

R1, R4 and R6 preferably represent a hydrogen atom.

Among the preferred derivatives according to the invention, R5 is advantageously a lower alkyl radical, preferably a methyl, an ethyl, an n-propyl or a perfluoromethyl, perfluoroethyl or perfluoropropyl radical, preferably perfluoroethyl.

Advantageously, X represents the divalent radical N—R7 and R7 represents a (lower) alkylcarbonyl radical.

Similarly, —Y═Z— is preferably a divalent radical of formula CR8═C and R8 represents a hydrogen atom or a (lower) alkylcarbonyl radical.

When R5 and R6 together form part of a ring of formula —$(CH_2)_m$—CW—, the carbonyl or thiocarbonyl —CW— is directly linked to the nitrogen and the radical —$(CH_2)_n$— is, for its part, linked to the carbonyl or thiocarbonyl of the group —CW—R5.

The present invention also relates to the process for the preparation of the derivatives of general formula I, as defined above.

The derivatives according to the invention may be obtained by reacting the corresponding amine of general formula II

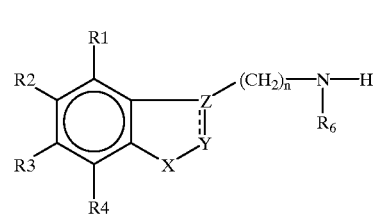

X, Y, Z, n, R1 to R4 and R6 being defined above, with a suitable acylating agent, according to the usual techniques for the preparation of amides, so as to introduce the radical

—CW—R5,

W representing an oxygen atom and R5 being defined above, with the corresponding halide or anhydride, or alternatively with activation of the corresponding acid optionally with a coupling agent, as employed in peptide synthesis.

The derivatives for which R5 and R6 together form part of a ring of formula —$(CH_2)_n$—CW—, with W representing an oxygen atom, are prepared by acylating the derivative of general formula II for which R6 represents a hydrogen atom, with a suitable acylating agent so as to introduce the radical —CW—$(CH_2)_n$—CW—O-alkyl, W representing an oxygen atom and n being defined above, and then to cyclize the amide obtained by a suitable reaction, for example by acid catalysis in the presence of traces of para-toluenesulphonic acid in xylene.

The conversion of a compound of formula I in which W represents an oxygen atom into a compound of formula I in which W represents a sulphur atom is carried out by the treatment with a standard sulphurization reagent such as phosphorus pentasulphide or Lawesson's reagent.

The derivatives for which Y—Z represents a divalent radical of formula

and R8 represents a (lower) alkylcarbonyl radical, may also be prepared by hydrolysis of its cyclic precursor of general formula III

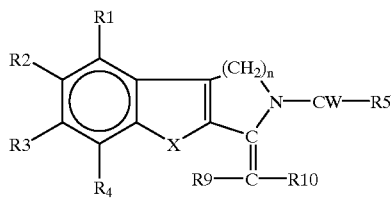

III in which X, n and R1 to R5 are defined above, R9 and R10 represent a hydrogen atom or a lower alkyl residue, or R9 and R10 together form a cycloalkyl in order to obtain the corresponding derivative of formula I in which R6 represents a hydrogen atom, and R8 represents a radical

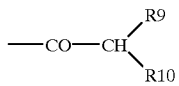

The derivative obtained above may then be converted in order to obtain a novel derivative of general formula I for which R6 is other than a hydrogen atom.

Other characteristics of the derivatives according to the invention and a process for their preparation will emerge on reading the examples which follow.

Starting Materials

The starting materials, corresponding to the general formulae II and III, are commercially available or may be obtained in particular according to the methods described below:

5-methoxytryptamine:

Supniewski et al., CA 55, 15458 (1961).

Melatonin:

Szmuskovics et al. J. Org. Chem., 25, 857 (1960),

Chem. and Eng. News, 45, 40 (1967).

Serotonin and melatonin naphthalenic analogues:

Andrieux J., Anker D., Mentzer C., Chim. Ther., 57 (1966),

Yous S., Andrieux J., Howell H. E., Morgan P. J., Renard P., Pfeiffer B., Lesieur D., Guardiola-Lemaitre B., J. Med. Chem., 35, 1484 (1992).

N-[2-(5-methoxy-2-oxo-2,3-dihydroindol-3-yl)ethyl]acetamide:

Szabo-Pusztay K., Szabo L, Synthesis, 276 (1979).

EXAMPLE 1

N-[2-(1-acetyl-5-methoxyindol-3-yl)ethyl]acetamide (1)

Melatonin (126 mg) is dissolved in tetrahydrofuran (10 ml) in a 50 ml round-bottomed flask, sodium hydride (200 mg) is then added and the mixture is maintained at reflux (10 min). After cooling (0° C.), acetyl chloride is added and the mixture is kept stirring overnight (room temperature). After filtration and dilution (EtOAc), the organic phase is washed with water and then separated on a silica plate. N-[2-(1-Acetyl-5-methoxyindol-3-yl)ethyl]acetamide (1) is mainly obtained, along with a side product, N-[2-(1-acetyl-5-methoxyindol-3-yl)ethyl]diacetamide (10) (cf. Example 10).

N-[2-(1-acetyl-5-methoxyindol-3-yl)ethyl]acetamide (1)

$^1$H NMR: CDCl$_3$: 1.96 (s, 3H, CH$_3$CO—Nβ); 2.49 (s, 3H, CH$_3$CO—Nα); 2.87 (t, 2H, CH$_2$); 3.56 (t, 2H, CH$_2$—N); 3.84 (s, 3H, CH$_3$O); 6.05 (broad s, 1H, NH); 6.91 (d, 1H, H-6); 6.96 and 7.19 (2s, 2H, H-4 and H-2); 8.24 (d, 1H, H-7); MS (m/z): 274 (M$^\oplus$.), 215, 173, 160 (100).

Exact mass: Calculated 274.1317 Found 274.1320.

EXAMPLE 2

N-[2-(2-acetyl-5-methoxyindol-3-yl)ethyl]acetamide (2)

Procedure A

1-Methylene-2-acetyl-6-methoxy-1,2,3,4-tetrahydro-β-carboline (100 mg) is dissolved in an acidic solution (HCl, 0.1 M, 10 ml) in a 25 ml round-bottomed flask, and the mixture is heated at 60° C. for one hour. The precipitate is filtered off and then washed with ether. N-[2-(2-Acetyl-5-methoxyindol-3-yl)ethyl]acetamide (2) is thus obtained.

Procedure B

To N-[2-(5-methoxyindol-3-yl)ethyl]diacetamide (4) (35 mg) dissolved in dichloromethane (3 ml), at 0° C., is added Meerwein's reagent (0.15 mmol, 0.15 ml). The mixture is maintained at room temperature for 12 h. The solution is filtered. A red precipitate is obtained. The precipitate is dissolved in methanol (1 ml). After reacting for 15 min, the methanol is evaporated off and the ethyl acetate is extracted out. N-[2-(2-Acetyl-5-methoxyindol-3-yl)ethyl]acetamide (2) is thus obtained, Yield=75%.

$^1$H NMR: cdcL$_3$: 1.90 (s, 3H, CH$_3$CO—Nβ); 3.29 (t, 2H, CH$_2$); 2.72 (s, 3H, 2-CH$_3$CO); 3.40 (t, 2H, CH$_2$—N); 3.97 (s, 3H, CH$_3$O); 7.11 (dd, 1H, H-6); 7.32 (broad s, 1H, NHCO); 7.39 (d, 1H, H-4); 7.47 (d, 1H, H-7); 10.63 (broad s, 1H, indole NH); MS (m/z): 274 (M$^\oplus$.), 215 (100), 202, 188, 160.

Exact mass: Calculated 274.1317 Found 274.1318.

EXAMPLE 3

N-[2-(2-acetyl-5-methoxyindol-3-yl)ethyl] propionamide (3)

The Procedure of Example 2 is repeated with 1-methylene-2-propionyl-6-methoxy-1,2,3,4-tetrahydro-β-carboline as starting material.

$^1$H NMR: CD$_3$COOD$_3$: 1.76 (t, 3H, CH$_3$ ethyl); 2.23 (t, 2H, CH$_2$ ethyl); 2.72 (s, 3H, CH$_3$CO in position 2 of the indole); 3.40 (t, 2H, CH$_2$); 3.57 (q, 2H, CH$_2$N); 3.95 (s, 3H, CH$_3$O); 7.10 (dd, 1H, H-6); 7.20 (broad s, 1H, NHCO); 7.40 (d, 1H, H-4); 7.5 (d, 1H, H-7); 10.6 (broad s, 1H, NH indole); MS (m/z): 288 (M$^\oplus$.), 245, 215 (100), 202, 188.

Exact mass: Calculated 288.1473 Found 288.1470.

EXAMPLE 4

N-[2-(5-methoxyindol-3-yl)ethyl]diacetamide (4)

Procedure A

Acetic anhydride (7 ml) is added with stirring to melatonin (500 mg) dissolved in benzene (50 ml). The mixture is heated for 72 h in refluxing benzene. The solvent is evaporated off and the crude product is taken up in water and then neutralized with sodium carbonate solution (pH>8). After extraction (dichloromethane), washing (water) and drying (magnesium sulphate), the crude product is flash-chromatographed (EtOAc eluent). N-[2-(5-Methoxyindol-3-yl)ethyl]diacetamide (4) (300 mg, 50% yield) is obtained.

Procedure B

Acetic anhydride (3 ml) is added with stirring to melatonin (380 mg). The mixture is heated for 4 h at 145° C. After evaporation of the acetic anhydride, the crude product is flash-chromatographed (50/50 EtOAc/petroleum ether eluent). The following are successively eluted:

-N-[2-(5-Methoxyindol-3-yl)ethyl]diacetamide (4) (180 mg, 40% yield).

$^1$H NMR: DMSO D$_6$: 2.30 (s, 6H, 2(CH$_3$CO)); 2.93 (t, 2H, CH$_2$); 3.81 (s, 3H, CH$_3$O); 3.89 (t, 2H, CH$_2$—N); 6.76 (d, 1H, H-6); 7.02 and 7.07 (2s, 2H, H-2 and H-4); 7.22 (d, 1H, H-7); 10.48 (broad s, 1H, NH); MS (m/z): 274 (M$^\oplus$.) 173 (100), 160, 145, 77.

Exact mass: Calculated 274.1317 Found 274.1320.
-N-[2-(2-acetyl-5methoxyindol-3-yl)ethyl]diacetamide (9),
-N-[-(1-acetyl-5-methoxyindol-3-yl)ethyl]diacetamide (10).

EXAMPLE 5

N-[2-(2-acetylindol-3-yl)ethyl]acetamide (5)

The procedure of Example 2 is repeated with 1-methylene-2-acetyl-1,2,3,4-tetrahydro-β-carboline as starting material.

$^1$H NMR: CDCl$_3$: 1.88 (t, 3H, CH$_3$CO); 2.58 (s, 3H, CH$_3$CO in position 2 of the indole); 3.27 (t, 2H, CH$_2$ in position 3 of the indole); 3.53 (t, 2H, CH$_2$—N); 6.68 (broad s, 1H, NHCO); 7.08 (t, 1H, H-7); 7.32 (m, 2H, H-5 and 6); 7.61 (d, IH, H-4); 10 (broad s, 1H, indole NH); MS (m/z): 244 (M$^\oplus$.), 185 (100), 172, 158, 130.

EXAMPLE 6

N-[2-(1-acetyl-2-oxo-5-methoxy-2,3-dihydroindol-3-yl)ethyl]acetamide (6)

Acetic anhydride (0.5 ml) is added with stirring to N-[2-(5-methoxy-2-oxo-2,3-dihydroindol-3-yl)ethyl]acetamide (120 mg) dissolved in benzene (5 ml). The mixture is heated for 1 h in refluxing benzene. The solvent is evaporated off and the crude product is separated on a silica plate. N-[2-(1-acetyl-2-oxo-5-methoxyindol-3-yl)ethyl]acetamide (6) is thus obtained.

$^1$H NMR: CD$_3$COOD$_3$: 1.84 (s, 3H, CH$_3$CO—Nβ); 2.30 and 2.94 (2m, 2H, CH$_2$), 2.57 (s, 3H, CH$_3$CO—Nα); 3.25 and 3.47 (2m, 2H, CH$_2$—N); 3.76 (t, 1H, H-3); 3.80 (s, 3H, CH$_3$O); 6.57 (d, 1H, H-6); 7.09 (s, 1H, H-4); 8.03 (d, 1H, H-7); 7.22 (broad s, 1H, NH).

EXAMPLE 7

N-[2-(5-Methoxyindol-3-yl)ethyl]glutarimide (7)

A mixture of 5-methoxytryptamine (420 mg) and diethyl glutarate (460 mg) is heated at 175° C. for 18 h. Separation on a column (EtOAc eluent) gives the corresponding ester amide.

The latter is treated with a trace of para-toluenesulphonic acid in xylene and the ethanol formed is removed using Dean-Stark apparatus. After refluxing for 9 h and separation on a silica plate, N-[2-(5-Methoxyindol-3-yl)ethyl] glutarimide (7) is obtained.

$^1$H NMR: CDCl$_3$: 1.88 (m, 2H, CH$_2$ β to the 2 CO): 2.62 (t, 4H, CH$_2$ α to the CO); 2.93 (t, 2H, CH$_2$ in position 3 of the indole); 3.90 (s, 3H, OCH$_3$); 4.05 (t, 2H, CH$_2$—NCO); 6.87 (dd, 1H, H-6); 7.03 (s, 1H, H-4); 7.20 (d, 1H, H-7); 8.0 (broad s, 1H, indole N—H). Mass spectrum (m/z): 286 (M$^\oplus$.), 173 (100), 160.

Exact mass: Calculated 286.1317 Found 286.1310.

EXAMPLE 8

N-[2-(2-Cyclohexylcarbonyl-5-methoxyindol-3-yl) ethyl]acetamide (8)

Repeating the procedure of Example 2, N-[2-(2-cyclohexylcarbonyl-5-methoxyindol-3-yl)ethyl]acetamide (8) is obtained.

$^1$H NMR: CDCl$_3$: between 1.30 and 1.80 (complex multiplet, 10H cyclohexyl); 1.91 (s, 3H, NCOCH$_3$); 3.30 (t, 2H, CH$_2$ in position 3 of the indole); 3.59 (t, 2H, CH$_2$—NCO); 3.81 (s, 3H, OCH$_3$); 6.72 (broad s, NHCO); 6.98 (d, 1H, H-6); 7.01 (s, 1H, H-4); 7.27 (d, 1H, H-7); 9.75 (broad s, 1H, indole N—H). Mass spectrum (m/z): 342 (M$^\oplus$.) 283 (100), 268, 188.

EXAMPLE 9

N-[2-(2-Acetyl-5-methoxyindol-3-yl)ethyl] diacetamide (9)

N-[2-(2-Acetyl-5-methoxyindol-3-yl)ethyl]diacetamide (9) is a side product in the acylation reaction of melatonin according to the process of Example 4, procedure B, isolated by flash chromatography.

$^1$H NMR: CDCl$_3$: 2.39 (s, 3H, CH$_3$CO—Nβ); 2.58 (s, 6H, CH$_3$CO—Nα); 3.35 (t, 2H, CH$_2$—Ar); 3.90 (s, 3H, CH$_3$O); 3.90 (t, 2H, CH$_2$—Nβ); 6.98 (dd, 1H, H-6); 7.12 (d, 1H, H-4); 7.29 (d, 1H, H-7); 8.85 (broad s, 1H, NH).

EXAMPLE 10

N-[2-(1-acetyl-5-methoxyindol-3-yl)ethyl] diacetamide (10)

$^1$H NMR: CDCl$_3$: 2.39 (s, 3H, CH$_3$CO—Nβ); 2.58 (s, 6H, CH$_3$CO—Nα); 2.94 (t, 2H, CH$_2$); 3.89 (s, 3H, CH$_3$O); 3.93 (t, 2H, CH$_2$—N); 6.95 (dd, 1H, H-6); 7.13 (d, 1H, H-4); 7.22 (s, 1H, H-2); 8.3 (d, 1H, H-6); MS (m/z): 316 (M$^\oplus$.), 215, 173 (100), 160.

EXAMPLE 11

N-[2-(5-Methoxy-2-oxo-2,3-dihydroindol-3-yl) ethyl]glutarimide (11)

145 mg of N-[2-(5-methoxyindol-3-yl)ethyl]glutarimide are dissolved in DMSO (30 µl) in a round-bottomed flask and concentrated HCl (72 µl) is added with stirring. The mixture is stirred overnight at room temperature. The crude product is neutralized with NH$_3$ and then extracted with EtOAc. After separation on a silica plate, N-[2-(5-methoxy-2-oxo-2,3-dihydroindol-3-yl)ethyl]glutarimide is obtained.

$^1$H NMR: CDCl$_3$: 1.82, (m, 2H, CH$_2$ β to the 2 CO); 2.18 (2m, 2H, CH$_2$), 2.52 (t, 4H, CH$_2$ α to the CO); 3.47 and 3.85 (2m, 2H, CH$_2$—N); 3.78 (s, 3H, OCH$_3$); 4.09 (t, 1H, H-3); 6.97 (m, 2H, H-6, H-7); 6.91 (s, 1H, H-4).

EXAMPLE 12

N-[2-(6-Acetyl-5-methoxyindol-3-yl)ethyl] acetamide (12)

N-[2-(6-Acetyl-5-methoxyindol-3-yl)ethyl]acetamide is prepared by alkaline hydrolysis of N-[2-(6-acetyl-1-carbethoxy- 5-methoxyindol-3-yl)ethyl]acetamide in alcoholic potassium hydroxide.

$^1$H NMR: CDCl$_3$: 1.89, (s, 3H), 2.61 (s, 3H); 2.88 (t, 2H); 3.43 (q, 2H); 3.90 (s, 3H); 6.25 (broad s, 1H); 6.95 (s, 1H); 7.06 (s, 1H); 7.76 (s, 1H); MS (m/z): 274 (M$^\oplus$.), 215, 202(100)

EXAMPLE 13

N-[2-(6-Acetyl-1-carbethoxy-5-methoxyindol-3-yl) ethyl]acetamide (13)

The first step of the synthesis is a carboethoxylation of melatonin with ethyl chloroformate in the presence of sodium hydroxide and tetrabutylammonium hydrogen sulphate. Acetylation of the product obtained with acetyl chloride in the presence of aluminium chloride in dichloroethane leads, after hydrolysis, to N-[2-(6-acetyl-1-carbethoxy-5-methoxyindol-3-yl)ethyl]acetamide.

$^1$H NMR: CDCl$_3$: 1.48, (s, 3H, CH$_3$ carbamate), 1.98 (s, 3H, CH$_3$ amide); 2.64 (s, 3H, CH$_3$ methylketone); 2.89 (t, 2H, CH$_2$-indole); 3.58 (t, 2H, CH$^2$—N); 3.95 (s, 3H, CH$_3$O); 4.47 (q, 2H, CH$_2$ carbamate); 5.88 (broad s, 1H, N—H); 6.99 (s, 1H, H-4); 7.45 (s, 1H, H-2); 8.4 (s, 1H, H-7). MS (m/z): 346 (M$^\oplus$.), 287 (100), 272, 202

EXAMPLE 14

N-[2-(1-carbethoxy-2-acetyl-5-methoxyindol-3-yl) ethyl]acetamide (14)

1-Methylene-2-acetyl-9-carbethoxy-6-methoxy-β-carboline (100 mg) is dissolved in acidic solution (HCl 0.1 M, 10 ml) in a round-bottomed flask (25 ml) and the mixture is heated at 60° C. for one hour. The precipitate is filtered off and then washed with ether. N-[2-(1-Carbethoxy-2-acetyl-5-methoxyindol-3-yl)ethyl]acetamide is thus obtained.

$^1$H NMR: CDCl$_3$: 1.45 (t, 3H); 1.92 (s, 3H); 2.45 (s, 3H); 2.84 (t, 2H); 3.49 (t, 2H); 3.83 (s, 3H); 4.47 (q, 2H); 7.0–7.06 (m, 3H); 7.92 (d, 1H); MS (m/z): 346 (M$^\oplus$.), 287, 215, 202(100)

EXAMPLE 15

N-[2-(2-acetyl-6-ethyl-5-methoxyindol-3-yl)ethyl] acetamide (14)

1-Methylene-2-acetyl-7-ethyl-6-methoxy-β-carboline (100 mg) is dissolved in acidic solution (HCl, 0.1 M, 10 ml) in a round-bottomed flask (25 ml) and the mixture is heated at 60° C. for one hour. The precipitate is filtered off and then washed with ether. N-[2-(2-Acetyl-6-ethyl-5-methoxyindol-3-yl)ethyl]acetamide is thus obtained.

$^1$H NMR: CDCl$_3$: 1.22 (t, 3H); 1.91 (s, 3H); 2.60 (s, 3H); 2.72 (q, 2H); 3.27 (t, 2H, CH$_2$); 3.52 (t, 2H); 3.86 (s, 3H); 6.97 (broad t, 1H); 7.15 (s, 1H); 7.31 (s, 1H); MS (m/z): 302 (M$^\oplus$.), 243 (100), 259, 230, 216

EXAMPLE 16

N-[2-(1-acetyl-5-methoxyindolin-3-yl)ethyl] acetamide (16)

To a solution, cooled to 0° C., of melatonin (1 mmol) in trifluoroacetic acid (2 ml) is added dropwise borane (2 eq, 1M solution in THF). The mixture is stirred for 30 min at 0° C. followed by dropwise addition of water (1.5 ml), and the medium is left stirring for 1 h at room temperature. The mixture is then brought to pH=10 using 2N potassium hydroxide solution and is then extracted with dichloromethane. The crude product is separated on a column of flash silica (25/75/5 acetone/dichloromethane/methanol) and 110 mg of N-[2-(5-methoxyindolin-3-yl)ethyl] acetamide are obtained, which product is then acetylated with acetic anhydride in pyridine to give N-[2-(1-acetyl-5-methoxyindolin-3-yl)ethyl]acetamide.

$^1$H NMR: CDCl$_3$: 1.65 (m, 1H); 1.93 (s, 3H); 1.9 (m, 1H); 2.12 (s, 3H); 3.31 (m, 3H); 3.63 (m, 1H); 3.68 (s, 3H); 4.11 (2m, 1H); 6.49 (broad s, 1H); 6.66 (m, 2H); 8.02 (d, 1H) MS (m/z): 276 (M$^\oplus$.), 272, 204, 174, 160, 148(100)

EXAMPLE 17

N-[2-(1-acetyl-6-chloro-5-methoxyindolin-3-yl) ethyl]acetamide (17)

To a solution of N-[2-(1-acetyl-5-methoxyindolin-3-yl) ethyl]acetamide (0.29 mmol) in acetonitrile (1.5 ml) is added bis(trifluoroacetoxyiodobenzene) (PIFA 1.2 eq) and the medium is left stirring for 1 min at room temperature. Saturated sodium chloride solution (0.5 ml) is next added and, after 15 min, the mixture is diluted with dichloromethane (10 ml) and dried over magnesium sulphate. The crude product obtained after evaporation is chromatographed on a column of flash silica (5/95 methanol/dichloromethane) and N-[2-(1-acetyl-6-chloro-5-methoxyindolin-3-yl)ethyl]acetamide (70 mg) is thus obtained.

$^1$H NMR: CDCl$_3$: 1.65 (m, 1H); 1.91 (s, 3H); 1.9 (m, 1H); 2.12 (s, 3H); 3.31 (m, 3H); 3.63 (m, 1H); 3.80 (s, 3H); 4.11 (2m, 1H); 6.28 (broad s, 1H); 6.75 (s, 1H); 8.15 (d, 1H)

EXAMPLE 18

N-[2-(1-benzyloxycarbonyl-5-methoxyindolin-3-yl) ethyl]diacetamide (18)

N-[2-(5-Methoxyindolin-3-yl)ethyl]acetamide is prepared by the method described for the synthesis of N-[2-(1-acetyl-5-methoxyindolin-3-yl)ethyl]acetamide. The intermediate N-[2-(1-benzyloxycarbonyl-5-methoxyindolin-3-yl)ethyl]acetamide is prepared by reacting the N-[2-(5-methoxyindolin-3-yl)ethyl]acetamide with ethyl chloroformate in dichloromethane at 0° C. in the presence of triethylamine. The final acylation is carried out with acetic anhydride in refluxing toluene for 24 h, and allows N-[2-(1-trifluoromethanesulphonyl-5-methoxyindolin-3-yl)ethyl]diacetamide to be obtained.

$^1$H NMR: CDCl$_3$: 1.96 and 2.11 (2m, 2H); 2.32 (s, 6H); 3.28 (m, 1H); 3.53 (m, 1H); 3.71 (s, 3H); 3.74–3.80 (m, 2H); 4.13 (m, 1H); 5.20 (m, 2H); 6.72 (m, 2H); 7.35 and 7.8 (m, 6H) $^{13}$C(DEPT): 26.1(CH$_3$); 33.7(CH$_2$); 37.4(CH); 42.1 (CH$_2$); 52.8(CH$_2$); 55.3(CH$_3$) 66.6(CH$_2$); 110.3(CH); 112.4 (CH); 115.1(CH); 127.9(CH); 128.0(CH); 128.6(CH); 134.4 (C); 135.7(C); 136.2(C); 155.6(C); 170.0(CO); 172.6(CO)

EXAMPLE 19

N-[2-(1-trifluoromethanesulphonyl-5-methoxyindolin-3-yl)ethyl]diacetamide (19)

N-[2-(5-Methoxyindolin-3-yl)ethyl]acetamide is prepared by the method described for the synthesis of N-[2-(1-acetyl-5-methoxyindolin-3-yl)ethyl]acetamide. The intermediate N-[2-(1-trifluoromethanesulphonyl-5-methoxyindolin-3-yl)ethyl]acetamide is prepared by reacting N-[2-(5-methoxyindolin-3-yl)ethyl]acetamide with trifluoromethanesulphonic anhydride in dichloromethane at −78° C. in the presence of triethylamine. The final acylation is carried out with acetic anhydride in refluxing toluene for 24 h, and allows N-[2-(1-trifluoromethanesulphonyl-5-methoxyindolin-3-yl)ethyl]diacetamide to be obtained.

$^1$H NMR: CDCl$_3$: 2.01 (m, 2H); 2.41 (s, 6H); 3.42 (m, 1H); 3.66 (m, 1H); 3.79 (s, 3H); 3.86 (m, 1H); 3.95 (m, 1H); 4.36 (t, 1H); 6.79 (m, 2H); 7.33 (d, 1)

EXAMPLE 20

N-[2-(6-(1-acetyl-3-(N,N-diacetyl-2-aminoethyl)-5-methoxyindolin-2-yl)-5-methoxyindol-3-yl)ethyl] diacetamide (20)

The product is prepared according to the method described by Laronze et al. (Bull. Soc. Chim. Fr. 1966, vol 133, p39–50), followed by acetylation according to the procedure described for N-[2-(5-methoxyindol-3-yl)ethyl] diacetamide.

¹H NMR: CDCl₃: 2.03 (s, 3H); 2.37 (s, 12H); 2.45 (m, 2H); 2.96 (t, 2H); 3.0 (m, 1H); 3.73 (s, 3H); 3.78 (m, 4H); 4.00 (s, 3H); 5.59 (s, 1H); 6.64 (s, 1H); 6.70 (dd, 1H); 6.88 (s, 1H); 6.93 (d, 1H); 7.19 (s, 1H); 8.25 (d, 1H); 8.37 (broad s, 1H) MS (m/z): 590 (M⊕.), 345, 215, 173(100)

EXAMPLE 21

N-[2-(2-acetyl-7-methoxynaphth-1-yl)ethyl] acetamide (21)

N-[2-(2-Acetyl-7-methoxynaphth-1-yl)ethyl]acetamide is obtained by acid hydrolysis of 6-methoxy-1-methylene-2-acetyl-2-aza-1,2,3,4-tetrahydrophenanthrene, prepared according to the method described by Jacquesy et al. (PCT patent/Fr 95/01179).

¹H NMR: CDCl₃: 1.91 (s, 3H); 2.68 (s, 3H); 3.35 (t, 2H) 3.66 (q, 2H); 4.03 (s, 3H); 6.86 (broad s, 1H); 7.23 (dd, 1H); 7.48 (d, 1H); 7.7 (m, 3H)

EXAMPLE 22

N-[2-(carbethoxy-2-acetyl-5-methoxyindolin-3-yl) ethyl]acetamide (22)

The product N-[2-(1-carbethoxy-2-acetyl-5-methoxyindol-3-yl)ethyl]acetamide (100 mg) is dissolved in ethanol (10 ml) in a round-bottomed flask (25 ml), 100 mg of Pd(OH)₂ are added and the mixture is stirred for 12 h at a normal pressure of hydrogen. After filtration, N-[2-(1-carbethoxy-2-acetyl-5-methoxyindolin-3-yl)ethyl] acetamide is obtained.

¹H NMR: CDCl₃: 1.27 (broad s, 3H); 1.50 (m, 1H); 1.92 (m, 7H); 3.45 (m, 2H); 3.78 (s, 3H); 4.30 (broad s, 2H); 4.83 (d, 1H); 6 (broad s, NH); 6.77 (m, 2H); 7.79 (broad s, 1H).

| Example | Name | Structural formula | Empirical formula Molar mass |
|---|---|---|---|
| 1 | 1AcMela | | C₁₅H₁₈N₂O₃ 274.31 |
| 2 | 2AcMela | | C₁₅H₁₈N₂O₃ 274.31 |
| 3 | 2aAcMela | | C₁₆H₂₀N₂O₃ 288.34 |
| 4 | MELAG | | C₁₅H₁₈N₂O₃ 274.31 |
| 5 | 2Ac-TRYP | | C₁₄H₁₆N₂O₂ 244.29 |

-continued

| Example | Name | Structural formula | Empirical formula Molar mass |
|---|---|---|---|
| 6 | 1AC-2OXOMELA | | $C_{15}H_{18}N_2O_4$ 290.31 |
| 7 | MELA3G | | $C_{16}H_{18}N_2O_3$ 286.33 |
| 8 | 2cyAcMELA | | $C_{20}H_{26}N_2O_3$ 342.43 |
| 9 | 2Ac-MELA3 | | $C_{17}H_{20}N_2O_4$ 316.35 |
| 10 | 1Ac-MELA3 | | $C_{17}H_{20}N_2O_4$ 316.35 |
| 11 | 2-OXOMELA3G | | $C_{16}H_{18}N_2O_4$ 302.32 |
| 12 | 6AcMela | | $C_{15}H_{18}N_2O_3$ 274.31 |

-continued

| Example | Name | Structural formula | Empirical formula Molar mass |
|---|---|---|---|
| 13 | CBACMELA | | $C_{18}H_{22}N_2O_3$ 346.38 |
| 14 | CB2AcMela | | $C_{18}H_{22}N_2O_3$ 346.38 |
| 15 | 6Et2AcMela | | $C_{17}H_{22}N_2O_3$ 302.37 |
| 16 | 1AcDHMela | | $C_{15}H_{20}N_2O_3$ 276.33 |
| 17 | 6CHAcDHMela | | $C_{15}H_{18}N_2O_3Cl$ 310.78 |
| 18 | CBDHMela3 | | $C_{23}H26N_2O_3$ 410.46 |
| 19 | TFDHMela3 | | $C_{16}H_{19}N_2O_3SF_3$ 408.39 |

-continued

| Example | Name | Structural formula | Empirical formula Molar mass |
|---|---|---|---|
| 20 | 6DMela3 | | $C_{32}H_{35}N_2O_3$ 590.67 |
| 21 | 2-AcNaph2 | | $C_{17}H_{19}NO_3$ 285.34 |
| 22 | C2AcDHMela | | $C_{18}H_{24}N_2O_3$ 348.39 |

Biological Activity

The hypnotic and sedative effects of the derivatives according to the invention, prepared above (whose test results are indicated in Table I below), were compared with those of two reference products, diazepam and melatonin, in 10- to 15-day-old chicks of the strain chair label JA657. The animals are subjected to programmes of alternating lighting consisting of 12 h of darkness (8.00 pm to 8.00 am) and 12 h of light (8.0 am to 8.00 pm). The room temperature is 25° C. for the first week that the chicks are reared and 22° C. from the second week onwards. During the day, the light is provided by a 100 W lamp placed 30 cm above the floor of the vivarium. During the tests, the live weight of the chicks varied between 95 and 155 g. The tests are carried out starting at 2.00 pm. The chicks are allotted into groups of 3 in identical 30 cm×50 cm×30 cm vivariums. The test products are administered intramuscularly (IM) into the pectoralis major muscle, in aqueous-ethanolic solution (ethanol/distilled water mixture, 50/50 V/V), at a rate of 0.2 ml of ethanolic solution per 100 g of live weight. The doses administered for the test products (novel compounds of the invention and reference substances) are equimolar (2 $\mu$M/100 g of live weight). The placebo corresponds to 0.2 ml of the ethanol/distilled water mixture (aa). Since ethanol is used as solvent, its effect was compared beforehand with that of physiological saline (NaCl solution at 0.9 p. 100) or distilled water.

The aqueous-ethanolic solutions of the test products were prepared at the time of use by successive dilution of an accurately weighed stock solution, obtained from 20 $\mu$M of product, to which is added 1 ml of pure ethanol, stirred by ultrasound and then made up to 2 ml with 1 ml of distilled water for an injectable preparation. The results obtained after IM administration of 2 $\mu$m mol of the test products, as a solution in 0.2 ml of the ethanol/distilled water mixture, per 100 g of live weight are presented in Table I. For each chick, the volume injected is adjusted, as a function of the actual live weight, to 0.2 ml per 100 g of live weight.

The parameters observed are the locomotor activity and the state of wakefulness of the chicks for 2 h, i.e. the equivalent of 6 theoretical wake-sleep cycles for a chick of this age. They are recorded by video camera over 120 minutes.

Five stages of alertness were defined:

stage 1: active wakefulness;

stage 2: prostrate animal, head maintained with tonicity, eyes open;

stage 3: light sleep, animal drowsy, eyes closed with intermittent opening, immobile posture not modified by stimulation;

stage 4: deep prostrate sleep: neck relaxed, characteristic posture with head under the wing or hanging backwards;

stage 5: standing sleep: eyes closed, immobile, head hanging down (catatonic).

These five stages correspond approximately to the stages of alertness and sleep defined on examining the electroencephalographic traces in this species. The correspondence is as follows:

deep prostrate sleep: stage 4="slow wave sleep" (SWS)

standing sleep: "sleep-like state I" (SLSI)

Stage 3, drowsy, could correspond to phases of paradoxal sleep, with movement of the head, for example.

The chicks are observed by a trained observer with continuous video control for at least 1 hour after the animals have woken up.

Two stimuli were used to confirm the observations of the behaviour of the chicks at regular intervals:

the noise caused by the shock of a plastic object on the glass of the vivarium, comparable to that of a chick's beak on the glass, corresponds to a moderate stimulus. It is carried out at each observation period (i.e. every 5 minutes);

and the presentation of a metal feeding container filled with the usual food, left in the vivarium for 2 minutes. This is a powerful stimulus which calls upon vision, hearing and smell. It is carried out every 15 minutes, that is to say at least 6 times for each test.

Wakefulness is defined by the appearance of the conscious elaborate behaviour of searching for and consuming food or drink.

The sleep time (ST) is defined by the sum of the durations of the phases of light sleep (stage 3), deep sleep (stage 4) and standing sleep (stage 5). The sedation time corresponds to the sum of the various times of active wakefulness during the observation period of 120 minutes.

The falling-asleep time (FAT) is equal (to within one minute) to the time required to pass from a state of active wakefulness (stage 1) to a non-alert state (stages 3, 4 and 5).

The hypnotic and sedative effects of the test products on the diurnal activity of 10- to 15-day-old chicks subjected to a programme of permanent light from birth to the 6th day, and then to a programme of alternate lighting of 12 h of day (8.00 am–8.00 pm) and 12 h of darkness (8.00 pm–8.00 am), are reported in Table I below.

Each series of tests starts at 2.00 p.m. For each test product, several series of measurements were made on batches of 3 animals, each value indicated being the average of 1 or more batches of 3 animals.

The following values were measured:

FAT: falling-asleep time equal to the time required to pass from the state of active wakefulness to a non-alert state;

ST: sleep time, equal to the duration of the period of sleep ranging from falling asleep to waking up;

Sedation time: sum of the various times of active wakefulness during the observation period of 120 minutes.

TABLE IV

| COMPOUND | DOSE ($\mu$M/100 g) | FAT (minutes) | ST (minutes) | Sedation time (minutes) |
| --- | --- | --- | --- | --- |
| 1 | 2 | 5–8 | 55–85 | 80–95 |
| 2 | 2 | 4–5 | 49–92 | 89–97 |
| 4 | 2 | 6–7 | 55–97 | –95–102 |
| 6 | 2 | 5–10 | 70–75 | 75–90 |
| 9 | 2 | NA–15 | 0–30 | 37–60 |
| 16 | 2 | 13–15 | 20–45 | 38–73 |
| 20 | 2 | 4–5 | 25–68 | 40–68 |
| 21 | 2 | 5–7 | 70–75 | 75–87 |
| Melatonin | 2 | NA | 0 | 65–105 |
| Diazepam | 2 | 2–5 | 81–100 | 95–115 |
| Placebo | 0 | NA | 0 | 30–65 |

N/A = not applicable, the animals remain alert.

The results obtained show, for the derivatives according to the invention, a higher hypnotic effect than that of the reference products (melatonin) and equivalent to that of diazepam.

The derivatives according to the invention are thus particularly advantageous for the treatment of diseases associated with disorders of melatonin activity.

The present invention thus relates to the derivatives of general formula I, as defined above, for their therapeutic use, in particular for the treatment of depression and psychiatric disorders, in particular stress, anxiety, depression, insomnia, schizophrenia, psychosis and epilepsy, and also for the treatment of sleeping disorders associated with travelling ("jet lag"), neurodegenerative diseases of the central nervous system such as Parkinson's disease or Alzheimer's disease, for the treatment of cancers, or alternatively as a contraceptive or as an analgesic.

The melatonin analogues according to the invention are also useful for the treatment of benign hyperplasia of the prostate, skin cancers, skin complaints such as psoriasis and acne, mycosis and glaucoma, as well as for increasing immune resistance.

They are also useful for preventing the symptoms of menopause, pre-menstrual syndromes, effects of ageing and sudden death syndrome in the newborn.

They are also useful in veterinary application to regulate birth in ruminants.

The present invention thus also relates to the pharmaceutical compositions adapted for administration of the derivatives of general formula I, in particular via the oral, parenteral or rectal route, in the form of wafer capsules, tablets, gelatin capsules, drinkable solutions, injectable solutions, including delay forms and sustained-release dressings for transdermal administration of the active principle, nasal sprays, or topical formulations (cream, emulsion, etc.), comprising a derivative of general formula I according to the invention and at least one pharmaceutically acceptable excipient.

The pharmaceutical compositions according to the invention are advantageously dosed to deliver the active principle in a single "intake".

For an oral administration, the effective unit doses are between 0.1 $\mu$g and 500 mg.

For an intravenous administration, the effective unit doses are between 0.1 $\mu$g and 100 mg.

The melatoninergic analogues according to the invention are also useful in cosmetics, in particular for protecting the skin against ageing, and also against hair loss.

The present invention thus also relates to a cosmetic composition comprising a derivative of general formula I according to the invention.

The cosmetic compositions according to the invention are formulated in a manner which is suitable for their topical application, in particular in one form of salves, creams, emulsions, ointments, lotions, etc.

What is claimed is:

1. The compound N-(2-(2-acetyl-7-methoxynaphth-1-yl)ethyl)acetamide.

2. A pharmaceutical composition, comprising a compound according to claim 1 and at least one pharmaceutically acceptable excipient.

3. A method of inducing sedation in a subject, said method comprising administering to said subject an amount of the pharmaceutical composition of claim 2 sufficient to induce a sedative effect in said subject.

4. A cosmetic composition, comprising a compound according to claim 1 in a form of a cream, a salve, an emulsion, an ointment, or a lotion.

* * * * *

UNITED STATES PATENT AND TRADEMARK OFFICE
CERTIFICATE OF CORRECTION

PATENT NO.: 6,140,372

DATED: October 31, 2000

INVENTOR(S): Jean-Berard FOURTILLAN, Marianne FOURTILLAN, Jean-Claude JACQUESY, Marie-Paule JOUANNETAUD, Bruno VIOLEAU, and Omar KARAM It is certified that an error appears in the above-identified patent and that said Letters Patent is hereby corrected as shown below:

On the Title Page, Item [54], in the Title, line 2, after "ANALOGUES", insert
--; PROCESS FOR THEIR PREPARATION--.

On the Title Page, Item [73], in the Assignee, line 2, "Cemaf" should read
--CEMAF--; and
line 2, "Isovesco" should read --Iscovesco--.

Signed and Sealed this

Fifteenth Day of May, 2001

*Attest:*

NICHOLAS P. GODICI

*Attesting Officer*   Acting Director of the United States Patent and Trademark Office